(12) United States Patent
Liedloff

(10) Patent No.: US 6,204,416 B1
(45) Date of Patent: Mar. 20, 2001

(54) METHOD FOR THE TRANSFORMATION OF CIS- AND TRANS-CYCLODODECENE OXIDE INTO CYCLODODECANONE

(75) Inventor: Haans-Joerg Liedloff, Domat/Ems (CH)

(73) Assignee: EMS-Chemie AG, Domat/Ems (CH)

( * ) Notice: Subject to any disclaimer, the term of this patent is extended or adjusted under 35 U.S.C. 154(b) by 0 days.

(21) Appl. No.: 09/538,429

(22) Filed: Mar. 29, 2000

(30) Foreign Application Priority Data

Apr. 8, 1999 (DE) .............................................. 199 15 894

(51) Int. Cl.$^7$ .......................... C07C 45/00; C07C 49/105
(52) U.S. Cl. ........................ 568/361; 568/338; 568/366; 568/375
(58) Field of Search ................................... 568/361, 338, 568/375

(56) References Cited

U.S. PATENT DOCUMENTS 3,786,099 * 1/1974 Howell .

5,892,123 * 4/1999 Anderson et al. .

OTHER PUBLICATIONS

Arata et al., "Isomerization of Cyclooctene and Cyclodocene Oxides Catalyzed by Solid Acids and Bases", Bulletin of th Chemical Society of Japan (1994), 67(8), p 2351–2353.*

* cited by examiner

*Primary Examiner*—Johann Richter
*Assistant Examiner*—Sikarl A. Witherspoon
(74) *Attorney, Agent, or Firm*—Jiawei Huang; J C Patents

(57) ABSTRACT

A method for the transformation of cis- and trans-cyclododecene oxide into cyclododecanone, comprising carrying out the reaction with catalytically activated hydrogen in the presence of a copper catalyst at a temperature of 150–260° C. and at a pressure in a range from atmospheric pressure to elevated pressure. The reaction proceeds via the intermediate products cyclododecen-3-ol and cyclododecen-3-one, and with cyclododecene being obtained as a by-product.

15 Claims, No Drawings

METHOD FOR THE TRANSFORMATION OF CIS- AND TRANS-CYCLODODECENE OXIDE INTO CYCLODODECANONE

BACKGROUND OF THE INVENTION

1. Field of the Invention

The subject matter of this invention is identified in the claims.

In particular, the subject matter of this invention concerns a method for the transformation of cis- and trans-cyclododecene oxide into cyclododecanone using catalytically activated hydrogen in the presence of a copper catalyst under the reaction conditions that will be described in more detail below, which leads to the formation of the intermediate products cyclododecen-3-ol and cyclododecen-3-one and of the by-product cyclododecene.

2. Description of the Related Art

Cyclododecanone is an intermediate product that forms in the course of the most frequently applied industrial method for the production of laurinlactam. Cyclododecanone can be obtained in various ways from the $C_{12}$ precursor cyclodoceda-1,5,9-triene. The only cyclododecanone synthesis which, as far as we are aware, is presently carried out comprises the catalytic hydrogenation of cyclododeca-1,5,9-triene to form cyclododecane, the oxidation of the cyclododecane by air to form mainly cyclododecanol and fluctuating quantities of cyclododecanone, and the subsequent catalytic dehydrogenation of the 12-ring alcohol to form the ketone.

In addition to this reaction sequence, the patent literature describes other methods which use cyclododeca-1,5,9-triene as the starting material and lead more or less directly to cyclododecanone. Thus, according to DE-AS 1058987 and the German Patent Specification No. DE-PS-1075601, cyclododecanone is produced by hydrogenating the cyclododecatriene oxide (=epoxycyclododecadiene) that was obtained by epoxidation from cyclododeca-1,5,9-triene to form cyclododecene oxide (=epoxycyclododecane) and the latter is subsequently rearranged to form cyclododecanone. However, this method has the drawback that the catalytic hydrogenation of cyclododecatriene oxide to form cyclododecene oxide does not have a sufficiently high selectivity. During this process, considerable quantities (approximately 10 wt %) of cyclododecanol and cyclododecane (approximately 5 wt %) form as by-products, both of which have to be discarded.

The method proposed in the patent SU 513966 appears to be especially simple in that it provides for a one-step synthesis of cyclododecanone from cyclododecatriene oxide. For this purpose, the unsaturated epoxide is hydrogenated in the presence of a nickel-aluminum-titanium catalyst. However, again, by-products that cannot be utilized for any other purposes form along with the cyclododecanol and the cyclododecane.

The inadequate selectivity of these two syntheses by way of cyclododecatriene oxide is apparently attributable to the fact that under the comparatively drastic reaction conditions necessary to hydrogenate the C—C double bond, the epoxide function triggers several secondary reactions at the same time.

SUMMARY OF THE INVENTION

Thus, the problem that this invention seeks to solve is to make available a method for the production of cyclododecanone which is based on a 12-ring epoxide and which does not lead to a by-product that cannot be used in the synthesis of the starting product or the final product.

This problem is solved by a method according to the present invention. According to the present invention, a method for the transformation of cis- and trans-cyclododecane oxide into cyclododecanone is characterized in that this reaction is carried out with catalytically activated hydrogen in the presence of a copper catalyst at a temperature of 150–260° C. and at a pressure in a range from atmospheric pressure to elevated pressure, that the reaction proceeds via the intermediate products cyclododecen-3-ol and cyclododecen-3-one, and that it leads to cyclododecene as a by-product.

Preferably, the copper catalyst contains 0.4–4wt % of chromium, 0.6–8 wt % of barium. and highly dispersed silicic acid or active aluminum oxide as the carrier substance.

Preferably, the copper catalyst consists substantially of copper or a copper compound and zinc oxide.

Preferably, the temperature is in a range from 180–240° C.

Preferably, the pressure is in a range from atmospheric pressure to $5 \times 10^5$ Pa.

Preferably, the cyclododecene which is formed as a by-product is separated and used to produce cis- and trans-cyclododecene oxide.

Preferably, the production of cyclododecanone from cis- and trans-cyclododecene oxide is carried out either as a batch process or as a continuous process.

DESCRIPTION OF PREFERRED EMBODIMENTS

Surprisingly, the problem was solved by reacting cis- and trans-cyclododecene oxide at a temperature from 150–260° C. and a pressure in a range from atmospheric pressure to excess pressure with catalytically activated hydrogen in the presence of a copper catalyst, in the course of which the targeted product, cyclododecanone, is formed by way of the intermediate products cyclododecen-3-ol and cyclododecen-3-one. The principal by-product that forms is cyclododecene which is separated by distillation and used to produce cis- and trans-cyclododecene oxide.

To carry out the method according to this invention, two copper catalysts types A and B. have been shown to be especially useful;

A. Catalysts which, in addition to copper, contain 0.4–4 wt % of chromium, 0.6–8 wt % of barium, and highly dispersed silicic acid or active aluminum oxide, such as are described for example, in DE PS 1568317, and B. Catalysts which consist principally of copper or a copper compound and zinc oxide and which are also known from patent documents.

In addition to the components cited, these catalysts may also contain small quantities of other components which facilitate their manufacture, lower the manufacturing costs or enhance their mechanical strength.

The method according to this invention is preferably carried out at a temperature in a range from 150–260° C. and under atmospheric pressure or slightly increased pressure, with a temperature range between 180 and 240° C. and a pressure range up to $5 \times 10^5$ Pa being especially referred.

The starting material, cis- and trans-cyclododecene oxide, is accessible according to known processes by epoxidizing cis- and trans-cyclododecene. Liquid-phase epoxidation with hydrogen peroxide in the presence of tungsten trioxide (WO$_3$) or sodium hydrogen tungstate (NaHWO$_4$) or in the presence of other tungsten compounds as a catalyst is especially suitable for this purpose.

The cyclododecene isomers required in the production of cis- and trans-cyclododecene oxide are preferably obtained by partially hydrogenating cyclododeca-1,5,9-triene according to well-known methods, such as are described, for example, in BE 0745935, DE 1643801, or in U.S. Pat. No. 3,576,894.

Part of the cyclododecene introduced into the epoxidation stage is derived from the processing step according to this invention in which this cycloalkene is formed as a by-product. For this purpose, as a result of the high differences in the boiling points, cyclododecene can be easily separated by distillation as an overhead product from cyclododecanone and other products present in the reaction mixture. The product present in the largest quantity is cyclododecanol which is formed in small quantities (less than 4 wt %) by catalytic hydrogenation of cyclododecanone. The alcohol is separated from ketone in a second distillation column where it is obtained as the bottom product. It is recommended that the cyclododecanol thus obtained be returned into the processing step according to this invention where it is partially dehydrogenated to form cyclododecanone and, at the same time, generates part of the hydrogen required.

According to the method made available by this invention, the production of cyclododecanone can be carried out as a continuous process or as batch process. To carry out this method on an industrial scale with an annual capacity of more than 10,000 metric tons, however, only the continuous process can be used; of course, this includes all up- and downstream reaction and separation or purification steps.

The possibility of converting cis- and trans-cyclododecene oxide mainly into cyclododecanone by means of catalytically activated hydrogen in the presence of copper catalysts of types A and B specified above is especially surprising in view of the fact that the relevant literature claims that such catalysts have a high activity only when primary and secondary alcohols are dehydrogenated to form aldehydes and ketones. In this context, reference should be made to DE-PS 1568317 and to the brochure of Sued-Chemie AG (Munich): "Catalysts of Sued-Chemie AG: Dehydrogenation of Alcohols."

To gather more detailed information about this unexpected reaction, a number of batch experiments were carried out. Using this approach, it is easiest to identify potential intermediate products and to determine the sequence of their formation. To analyze each reaction mixture, gas chromatography alone and gas chromatography in association with mass spectrometry (GC/MS) were used. These studies demonstrated that the reaction of cis- and trans-cyclododecene oxide (C$_{12}$H$_{22}$O) into the structurally isomeric cyclododecanone (C$_{12}$H$_{22}$O) does not take place in one step but in three steps by way of cyclododecen-3-ol (C$_{12}$H$_{22}$O) and cyclododecen-3-one (C$_{12}$H$_{20}$O). The unsaturated ketone almost certainly forms as a result of the dehydrogenation of the unsaturated alcohol, and cyclododecanone is the result of the dehydrogenation of cyclododecen-3-one. It is still not clear how cyclododecen-3-ol forms from cis- and trans-cyclododecene oxide. It is also completely unknown how cyclododecene forms. What is known is that none of the reactions mentioned take place in the absence of catalytically activated hydrogen. Heating cis- and trans-cyclododecene oxide in contact with the copper catalysts mentioned only leads to the gradual formation of undefined decomposition products.

The formation of cyclododecen-3-ol and cyclododecen-3-one as intermediate products appears to indicate that by choosing suitable reaction conditions, it might be possible to obtain these unsaturated compounds as the main products.

In addition, it can be assumed that the quantity of the by-product cyclododecene can be decreased principally by means of optimizing the copper catalysts.

The examples below will describe this invention in greater detail without, however, intending to limit its scope in any way.

a) Continuous Experiments

The continuous reaction of cis- and trans-cyclododecene oxide to form cyclododecanone and cyclododecene was carried out in a vertically upright tubular reactor in which the fluid flows upward from the bottom and which has the following dimensions:

| | |
|---|---|
| Inside diameter of the reactor: | 64 mm |
| Length of the reactor to the overflow port: | 760 mm |
| Diameter of the perforated central guide tube for holding the thermoelement: | 10 mm |
| Maximum reactor capacity for catalyst pellets: | 1750 cm$^3$ |

The reactor was heated via a double-walled jacket by means of heat transfer oil.

Using a metering pump, the educt was introduced into the reactor from a distillation receiver rendered inert and heated to 100° C. Between the pump and the reactor inlet, a heater was installed, in which the educt was heated to the reaction temperature.

Also at the bottom of the reactor, the inlet for the hydrogen or, alternatively, the nitrogen or H$_2$/N$_2$ mixtures was provided. The gas currents (measured in m$_n^3$) were roughly adjusted by setting the preliminary pressure on the gas bottles and finely attuned by means of the needle valve on each rotameter.

The liquid reaction mixture exited the reactor via the overflow port and passed from there into a container that had also been heated to 100° C.

The waste gases, mainly hydrogen, were exhausted from the reactor and the product container via a cooler and a waste gas line and released outdoors.

Entrained cyclododecene, cyclododecanone, and water that formed during the formation of cyclododecene were condensed in the cooler.

All components of the test apparatus were made of steel.

The test procedure is described below:

First, the apparatus was thoroughly rinsed with nitrogen and heated to the operating temperatures.

Subsequently, the metering pump for cyclododecene oxide was switched on, and the reactor was filled at a high speed (approximately 5 kg/h) with the starting material up to the overflow port. As soon as the overflow port was reached, the flow rate was immediately reduced to the desired flow rate. Next, the hydrogen current was switched on and adjusted to the specified flow rate. Approximately 4 h after the hydrogen current had been added, the first sample was taken by way of a sampling device that was attached to the overflow port, and additional samples were taken every hour on the hour thereafter. From approximately the 8th hour after the hydrogen current had been switched on, a gas chromatographic analysis of these samples showed that they had an approximately constant composition. From this time on, the reactor had reached a steady-state operation. The pressure in the reactor corresponded to the atmospheric pressure.

Batch Experiments

The batchwise reaction of cis- and trans-cyclododecene to form cyclododecanone and cyclododecene was carried out in a glass apparatus with a cylindrical reactor component and the relevant connecting devices, i.e., an inlet tube for hydrogen or nitrogen which extended all the way down to the bottom of the reactor, openings for the thermometer, the gas discharge tube, the educt inlet, and the sampling device. The reactor component had a capacity of approximately 50 cm$^3$ for the catalyst.

The reactor was heated by means of an oil bath.

The tests carried out are described below:

The reactor which was filled with catalyst pellets was rendered inert and heated to the reaction temperature. The reaction was subsequently started by rapidly adding the educt which had also been heated to the reaction temperature and by possibly adding the hydrogen flow at the same time. The quantity of hydrogen to be added was adjusted in the same way as in the continuous experiments.

At the specified times, samples for the purpose of analysis were taken by means of a pipette.

c) Methods of Analysis c1) Gas chromatography

A gas chromatograph from Hewlett-Packard, Type HP6890, and a 30 m capillary column, Type DB17MS, of J&W-Scientific (Folsom, USA) were used.

c2) Gas chromatography/mass spectrometry

Gas chromatograph, Type 5890/Series 2, and mass spectrometer, Type 5971A, both from Hewlett-Packard. Column: same as above. Authentic samples of the individual substances were used as references.

d) Materials

The mixture of cis- and trans-cyclododecene oxide was purchased from Fluka AG (Buchs/Switzerland).

The Type B copper catalyst used was purchased from Sued-Chemie AG (Munich, Germany). This was the prereduced Type T-4427B in the form of pellets.

| Composition: | CuO: | 30 wt % |
|---|---|---|
| | ZnO: | 64 wt % |
| | Remainder: | binding material |

Bulk Density: Approximately 0.85 kg/L,

The Type A copper catalyst was purchased from HÜLS (Marl, Germany). This catalyst was Type H-1044 in the form of pellets.

| Composition: | CuO: | 27 wt % |
|---|---|---|
| | BaCrO$_4$: | 8 wt % |
| | Cr$_2$O$_3$: | 1 wt % |
| | SiO$_2$: | 62 wt % |

Bulk Density: Approximately 0.55 kg/L,

The abbreviations used in the examples have the following expansion:

| CDOL: | cyclododecanol |
|---|---|
| CDON: | cyclododecanone |
| CDEN: | cyclododecene (cis- and trans-) |
| CDOX: | cyclododecene oxide (cis- and trans-) |
| CDENOL: | cyclododecen-3-ol (cis- and trans-) |
| CDENON: | cyclododecen-3-one (cis- and trans-) |
| GC/MS: | gas chromatography/mass spectrometry |

EXAMPLE 1

Continuous

| Catalyst: | T-4427 B |
|---|---|
| Catalyst volume*: | 1.4 L |
| Reaction temperature: | 200° C. |
| Pressure: | atmospheric pressure |
| CDOX flow rate: | 0.8 kg/h |
| H$_2$ flow rate: | 0.5 m$_n^3$/h |

*The available reactor volume was not completely filled with catalyst pellets. The uppermost layer up to the overflow port consisted of glass beads which prevented the catalyst pellets from floating off.

By means of gas chromatography, the product was determined to have the following composition:

| CDON: | 73.3 wt % |
|---|---|
| CDEN: | 22 wt % |
| CDOL: | 3.4 wt % |
| CDOX: | — |
| Other: | 1.3 wt % |

EXAMPLE 2

Batchwise

| Catalyst: | T-4427 B |
|---|---|
| Catalyst quantity: | 30 g |
| Reaction temperature: | 200° C. |
| Pressure: | atmospheric pressure |
| CDOX quantity: | 5 g in 20 g of tetradecane as the solvent |
| H$_2$ flow rate: | 15 cm$_n^3$/min |

At the time intervals listed in Table 1, samples were taken and quantitatively and qualitatively analyzed by means of GC and GC/MS.

TABLE 1

Composition (in wt %, without solvent) of the reaction mixture as a function of the reaction time.

| Time [min]: | 0 | 3 | 6 | 10 | 20 | 40 | 60 |
|---|---|---|---|---|---|---|---|
| CDOX | 100 | 96.8 | 89 | 79.1 | 69.5 | 40.8 | 8.7 |
| CDON | — | 0.03 | 2.7 | 6.6 | 13.9 | 42.1 | 69 |
| CDEN | — | 0.03 | 0.4 | 1.9 | 4.2 | 11.1 | 19 |
| CDENOL | — | 3.1 | 7.8 | 12 | 11.5 | 4.2 | 0.7 |
| CDENON | — | 0.01 | 0.02 | 0.03 | 0.03 | 0.01 | 0 |
| CDOL | — | 0 | 0 | 0 | 0.3 | 0.7 | 1.2 |
| OTHERS | — | 0.03 | 0.08 | 0.27 | 0.57 | 1.19 | 1.4 |

EXAMPLE 3

Batchwise

In this experiment, the hydrogen is produced by dehydrogenation of CDOL.

| | |
|---|---|
| Catalyst: | H-1044 |
| Catalyst quantity: | 19 g |
| Reaction temperature: | 220° C. |
| Pressure: | atmospheric pressure |
| CDOX quantity: | 2.8 g (10%) |
| CDOL quantity: | 25.2 g (90%) |

The results of this test are summarized in Table 2.

TABLE 2

Composition of the reaction mixture as a function of the reaction time.

| Time [min]: | 0 | 3 | 6 | 10 | 20 | 40 | 60 |
|---|---|---|---|---|---|---|---|
| CDOX | 10 | 6.85 | 0.28 | 0 | 0 | 0 | |
| CDON | — | 10.1 | 66.5 | 89.6 | 95 | 94.8 | |
| CDEN | — | 1.0 | 4.1 | 4.05 | 4.0 | 3.9 | |
| CDENOL | — | 0.5 | 0.2 | 0 | 0 | 0 | |
| CDENON* | — | — | — | — | — | — | |
| CDOL | 90 | 81.4 | 29.1 | 5.9 | 0.14 | 0.07 | |
| OTHERS | — | 0.1 | 0.22 | 0.45 | 0.86 | 1.23 | |

*Concentration maximum of 0.007%

What is claimed is:

1. A method for the reaction of cis- and trans-cyclododecene oxide to form cyclododecanone, comprising carrying out the reaction with catalytically activated hydrogen in the presence of a copper catalyst at a temperature of 150–260° C. and at a pressure in a range from atmospheric pressure to elevated pressure, wherein the reaction proceeds via intermediate products cyclododecen-3-ol and cyclododecen-3-one, and leads to cyclododecene as a by-product.

2. The method as claimed in claim 1, wherein the copper catalyst contains 0.4–4 wt % of chromium, 0.6–8 wt % of barium, and highly dispersed silicic acid or active aluminum oxide as carrier substance.

3. The method as claimed in claim 1, wherein the copper catalyst consists substantially of copper or a copper compound and zinc oxide.

4. The method as claimed in claim 1, wherein the temperature is in a range from 180–240° C.

5. The method as claimed in claim 1, wherein the pressure is in a range from atmospheric pressure to about $5 \times 10^5$ Pa.

6. The method as claimed in claim 1, wherein the cyclododecene which is formed as a by-product is separated and used to produce cis- and trans-cyclododecene oxide.

7. The method as claimed in claim 1, wherein the production of cyclododecanone from cis- and trans-cyclododecene oxide is carried out either as a batch process or as a continuous process.

8. The method as claimed in claim 2, wherein the temperature is in a range from 180–240° C.

9. The method as claimed in claim 2, wherein the pressure is in a range from atmospheric pressure to about $5 \times 10^5$ Pa.

10. The method as claimed in claim 2, wherein the cyclododecene which is formed as a by-product is separated and used to produce cis- and trans-cyclododecene oxide.

11. The method as claimed in claim 2, wherein the production of cyclododecanone from cis- and trans-cyclododecene oxide is carried out either as a batch process or as a continuous process.

12. The method as claimed in claim 3, wherein the temperature is in a range from 180–240° C.

13. The method as claimed in claim 3, wherein the pressure is in a range from atmospheric pressure to about $5 \times 10^5$ Pa.

14. The method as claimed in claim 3, wherein the cyclododecene which is formed as a by-product is separated and used to produce cis- and trans-cyclododecene oxide.

15. The method as claimed in claim 3, wherein the production of cyclododecanone from cis- and trans-cyclododecene oxide is carried out either as a batch process or as a continuous process.

* * * * *